(12) United States Patent
Lidgren et al.

(10) Patent No.: US 6,448,315 B1
(45) Date of Patent: Sep. 10, 2002

(54) METHOD FOR THE PREPARATION OF UHMWPE DOPED WITH AN ANTIOXIDANT AND AN IMPLANT MADE THEREOF

(75) Inventors: Lars Lidgren, Lund; Peter Bengtsson, Göteborg; Peter Sjövall, Sandby; Bengt Wesslén, Staffanstorp, all of (SE)

(73) Assignee: Bone Support AB, Tollarp (SE)

( * ) Notice: Subject to any disclaimer, the term of this patent is extended or adjusted under 35 U.S.C. 154(b) by 0 days.

(21) Appl. No.: 09/890,077

(22) PCT Filed: Feb. 17, 2000

(86) PCT No.: PCT/SE00/00314

§ 371 (c)(1), (2), (4) Date: Dec. 27, 2001

(87) PCT Pub. No.: WO00/49079

PCT Pub. Date: Aug. 24, 2000

(30) Foreign Application Priority Data

Feb. 17, 1999 (SE) ................................................ 9900519

(51) Int. Cl.⁷ .............................. C08K 5/15; C08K 3/00
(52) U.S. Cl. ........................................ 524/110; 524/424
(58) Field of Search .................................. 524/110, 424

(56) References Cited

U.S. PATENT DOCUMENTS 5,797,873 A 8/1998 Franz et al.
5,827,904 A 10/1998 Hahn

FOREIGN PATENT DOCUMENTS

| CZ | 221404 | 4/1983 | ........... C07D/11/72 |
| EP | 0109310 | 5/1984 | ........... A61L/15/04 |
| EP | 0495284 | 7/1992 | ........... A61L/27/00 |
| EP | 0805178 | 11/1997 | ........... C08K/5/15 |
| EP | 0860467 | 8/1998 | ........... C08K/5/15 |
| EP | 0995449 | 4/2000 | ........... A61L/27/00 |
| SE | 464912 | 7/1991 | ........... A61L/27/00 |
| WO | WO 89/03695 | 5/1989 | ........... A61L/25/00 |
| WO | WO 00/02597 | 1/2000 | ........... A61L/27/00 |
| WO | WO 00/07639 | 2/2000 | ........... A61L/24/02 |

OTHER PUBLICATIONS

"Prevention of Fatigue Cracks in Ultrahigh Molecular Weight Polyethylene Joint Components By The Addition of Vitamin E," By Tomita et al.; J Biomed Mater Res (Appl Biomater), vol. 48 1999, pp. 474–478.

"Tribological Properties of Extruded, Pressed, and Modified Ultra–High Molecular Weight Polyethylene (UHMWPE)–A Ring–On–Disc Screening Test," By Huber et al.; American Society for Testing and Materials, 1998, pp. 130–137.

"Fatigue Wear Properties of Vitamin E Contained UHM-WPE," By Tomita et al.; Research Center for Biomedical Engineering, Kyoto University, p. 1280.

Primary Examiner—Kriellion A. Sanders
(74) Attorney, Agent, or Firm—James Ray & Associates

(57) ABSTRACT

The invention relates to a method for the preparation in a reactor of a UHMWPE material doped with an antioxidant, preferably vitamin E.

19 Claims, 1 Drawing Sheet

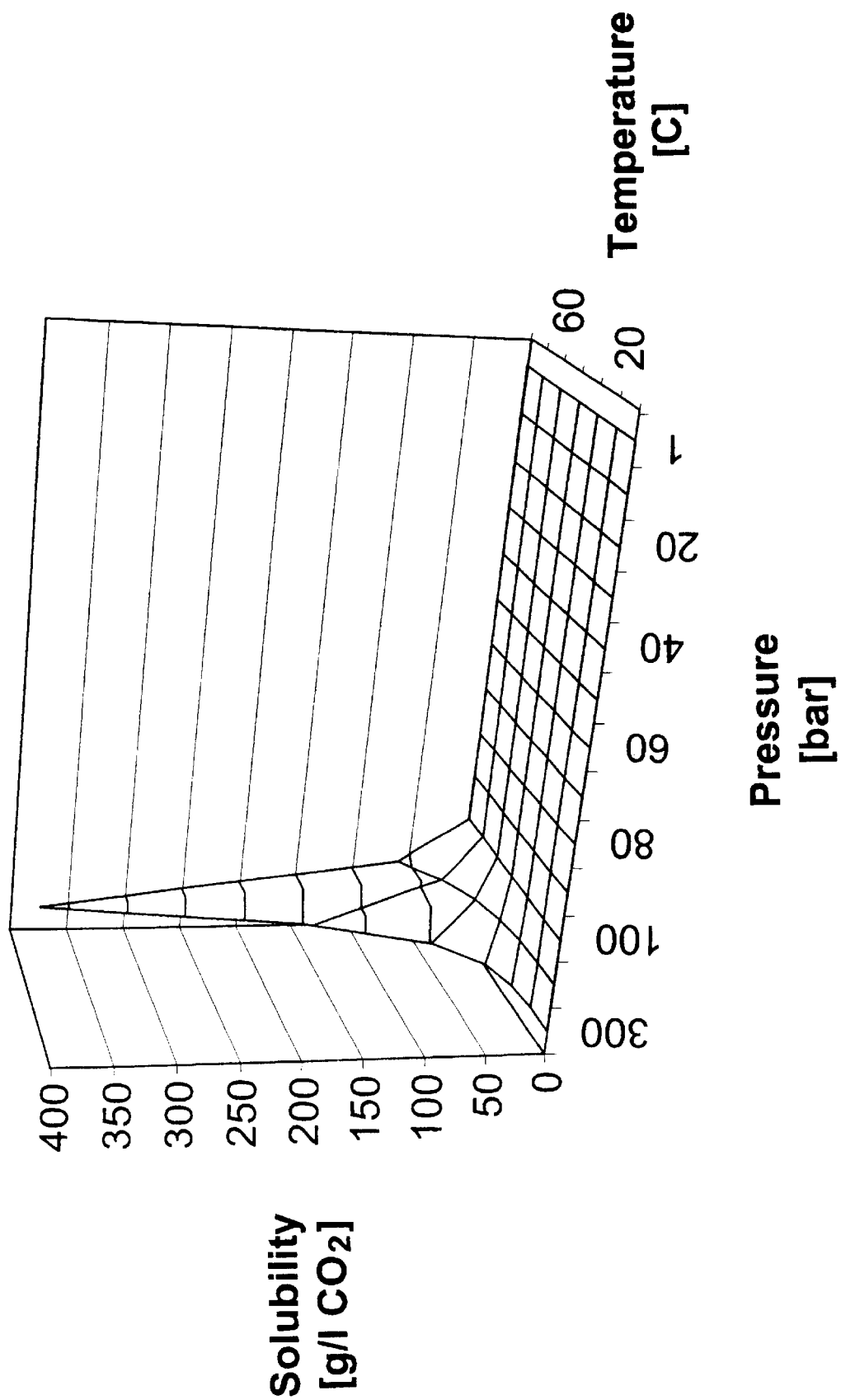

METHOD FOR THE PREPARATION OF UHMWPE DOPED WITH AN ANTIOXIDANT AND AN IMPLANT MADE THEREOF

TECHNICAL FIELD

The present invention relates to a method for the preparation of UHMWPE doped with an antioxidant, preferably vitamin E.

The invention also relates to an implant comprising UHMWPE doped with an antioxidant by using said method.

BACKGROUND ART

The majority of endoprosthetic joint replacements currently implanted in patients comprises a highly polished metal or ceramic component articulating on ultra high molecular weight polyethylene (UHMWPE) material. Although such combination of materials has been used over the last 30 years, the present clinical practice of using said prostheses in an increasing number of younger patients and older patients with longer life expectancy has generated renewed concern about the wear and durability of UHMWPE.

UHMWPE is a semicrystalline, linear homopolymer of ethylene, which is produced by stereospecific polymerization with Ziegler-Natta catalyst at low pressure (6–8 bar) and low temperature (66–80 C.). The synthesis of nascent UHMWPE results in a fine granular powder. The molecular weight and its distribution can be controlled by process parameters such as temperature, time and pressure. High wear resistance, high abrasion resistance, low coefficient of friction, high impact strength, excellent toughness, low density, biocompatibility and biostability are some of the properties that make UHMWPE an excellent material for implants. However, because of difficulties in fabrication by conventional techniques such as extrusion, injection molding or calendering, the use of UHMWPE has been limited. Due to the high molecular weight thereof, UHMWPE has a very high melt viscosity rendering it difficult or impractical to fabricate by the conventional melt processing techniques.

The major concern relating to the long term clinical performance of UHMWPE implants is adverse tissue reactions caused by the generation of UHMWPE debris. The particles of UHMWPE debris generated at the articulating surface are transported to the hard and soft tissues surrounding the joint. Billions of submicron particles are shed into the joint space leading to an inflammatory reaction with increased amount of joint fluid and pressure. Certain UHMWPE particles cause a macrophage mediated inflammatory response leading to bone resorption. When present around the neck of the femoral component, this type of bone resorption is a major cause for implant loosening, patient pain and the need for revision surgery.

In an effort to determine the cause of accelerated wear rates and premature component failures, studies have been conducted on material variables involved in component fabrication and utilization. Deformation and loosening of implants brought on by excessive wear rates has been correlated to γ-irradiation sterilization in air causing chain scission, which lowers the wear resistance and accelerates the degradation process.

Sterilization by γ-irradiation has been the method of choice for implants since about 1980. However, γ-sterilization generates free radicals, which react in the presence of oxygen to almost exclusively form peroxyl radicals.

These free radicals and peroxyl radicals react with PE chains and each other to form oxidative degradation products and additional radical species. This cycle of oxidation product and radical species formation has been shown to occur over several years as oxidation levels continuously increase in components over this time period. The resulting formation of chain scission products creates shorter molecular chains, degrading the mechanical properties and performance of UHMWPE implants. Furthermore, the damage caused by γ-irradiation does not require the implant to be exposed to levels of stress found in use. Instead, oxidative degradation of γ-irradiated components may occur during storage prior to implantation.

A recognized method of minimizing the wear rate while avoiding long-term oxidation of UHMWPE implants is to induce controlled amounts of crosslinking in the UHMWPE either by chemical or radiation techniques. Studies of the effects of high dose γ-irradiation of UHMWPE have been performed by H. McKellop, et al, at the J. Vernon Luck Orthopaedic Research Center, Orthopaedic Hospital, presented on the 44$^{th}$ Annual Meeting., Orthopaedic Research Society, in Mar. 16–19, 1998, New Orleans, La., USA. Extruded bars of UHMWPE were exposed to γ-irradiation in air at doses from 3.3 to 100 Mrad and remelted by heating in air to 150 C. and holding at 150 C. for 5 hours and then slow cooling to room temperature. It was concluded that the wear rate of the radiation crosslinked UHMWPE was decreased markedly with increasing. dose compared to the UHMWPE controls without crosslinking. Radiation crosslinking caused little or no change in yield strength, but, the ultimate strength elongation to failure and impact strength decreased with increasing radiation dose, indicating that an optimum crosslinking dose would be one which provides a substantial reduction in wear while maintaining acceptable levels of other physical properties. Additionally, it was concluded that remelting of the irradiated UHMWPE substantially reduced the residual free radicals. This method therefore provides a practical means for the production of UHMWPE implants on an industrial scale.

Another method of preventing oxidation in the manufacturing of UHMWPE implants has been carried out by Stark C., Sun D. C., Yau S. S., Pereira P., Schmidig G., Wang A., Dumbleton J. H., and was reported on the "Combined Orthopaedic Research Societies Meeting", Sep. 28–30, 1998, Hamamatsu, Japan. Said method involved a manufacturing process substantially oxygen-free from resin to final machining resulting in a product essentially free from oxidation.

Two other methods which have been recently employed are ion beam irradiation for a few minutes followed by annealing (remelting) at 150 C. (W. H. Harris, A. A. O. S., February., 1999, Anaheim, USA), and γ-irradiation in an inert environment followed by so called stabilization for five days at 50 C. (Dumbleton et al., A. A. O. S., 1999, Annaheim, USA).

Yet another known method to prevent oxidation in UHMWPE orthopaedic implants was presented in J. Jpn Orthop. Assoc. 72 (8), 1998, and involves the addition of a small amount of vitamin E to the polymer. In this method, UHMWPE was mixed with vitamin E (DL-α-Tocopherol) in an amount of 0.5 weight %. A 60×60×10 mm plate was formed by compression in a mold and treated by 2.5 Mrad γ-radiation in an environment of air. After treatment the plate was allowed to stand in room temperature, for 60 days and was subsequently oxidized in air at 220 C. for 10 hours. Fatigue tests showed that flaking damage and crack under the surface were inhibited by the addition of vitamin E.

As stated above, due to the high molecular weight thereof, UHMWPE has a very high melt viscosity rendering it difficult or impractical to fabricate by the conventional melt processing techniques. Consequently, it is further extremely difficult to obtain a homogenous mixture of UHMWPE with other substances.

In U.S. Pat. No. 5,827,904 a composition for the manufacture of medical implants is shown, which consists of a polymeric material in powder form and a carotenoid doped into the polymer to produce a oxidation-resistant matrix for forming the implant. In the doping process the carotenoid is dissolved solved in an organic solvent, such as 2-propanol, cyclohexane, n-hexane, benzene, and the like.

Even if the organic solvent is present in the soaking of the material to be doped, the use of volatile organic solvents is dangerous as many organic solvents are flammable and explosive. Furthermore, many organic solvents are toxic or carcinogenic and most so if inhaled. In addition, expensive "explosion proof" equipment must be used, such as static electricity control systems, explosion vents, reinforced equipment, solvent recovery systems and the like.

A method involving an organic solvent for the preparation of antioxidant doped UHMWPE to be used in an implant may also result in difficulties to remove all of the organic solvent, especially in the implant without at the same time damaging or destroying the same.

SUMMARY OF THE INVENTION

The object of the present invention is to provide an improved method for the addition of an antioxidant to UHMWPE in order to obtain a homogenous mixture of ultra high molecular weight polyethylene and an antioxidant.

A further object of the invention is to provide such a method enabling a solvent-free doping of UHMWPE with an antioxidant and hence the obtaining of an implant which is free of any residue of solvent.

These objects are achieved by a method having the characterizing features of claim 1. Favorable and preferred embodiments of the method are disclosed in claims 2–19.

In order to further explain the invention reference is given to the accompanying drawing in which FIG. 1 shows the solubility of vitamin E in $CO_2$ at different temperatures and pressures.

By mixing particles of UHMWPE with an antioxidant, preferably vitamin E, most preferably $\alpha$-tocopherol, in a solvent comprising $CO_2$ under supercritical fluid conditions at elevated temperature and pressure, a superfluid mixture being formed, and then evaporate $CO_2$ from the mixture, UHMWPE doped with an antioxidant being obtained.

In this connection the critical temperature is that temperature above which a gas cannot be liquefied by pressure alone. The pressure under which a substance may exist as a gas in equilibrium with the liquid at the critical temperature is the critical pressure. In the inventive method supercritical fluid conditions means that $CO_2$ is subjected to such a temperature and such a pressure that a supercritical fluid and thereby a superfluid mixture is obtained, the temperature being above the supercritical temperature, which for $CO_2$ is 31.3 C., and the pressure being above the supercritical pressure, which for $CO_2$ is 73.8 bar.

The antioxidant concentration of the UHMWPE material should be approximately 0.005–5.0 weight %, preferably approximately 0.1–1.0 weight %. The wear resistance of the UHMWPE doped with an antioxidant may be further improved by $\gamma$-irradiation at a dose above 2 Mrad, preferably above 9 Mrad, and by subsequently subjecting the UHMWPE so obtained to an elevated temperature, preferably above 80° C.

Another object is to provide an implant comprising UHMWPE doped with an antioxidant by using said method.

Apart from the fact that the method according to the invention results in doped particles without residual solvent, it also makes it possible to produce a doped implant without any toxic organic solvent.

The implant of the invention has excellent wear resistance and a decreased degradation before and after implantation in the body.

DETAILED DESCRIPTION OF THE INVENTION

The purpose of adding an antioxidant to UHMWPE is to reduce oxidation of the polymer during sterilization and post sterilization and thereby decrease the wear of the implant in the body. Sterilization with $\gamma$-radiation induces free radicals in the material and these radicals react with oxygen to produce peroxy radicals which attack the polymer chains. Chain scission drastically reduce the wear resistance of the polymer, for example, by lowering the molecular weight. Natural antioxidants can react with radiation induced free radicals in the polymer thereby terminating the chain scission process and in this way reduce the oxidation of the polymer. Examples of antioxidants which can be used in the method according to the invention include $\alpha$- and $\delta$-tocopherol; propyl, octyl, or dodecyl gallates; lactic, citric, and tartaric acids and their salts; as well as orthophosphates. Preferably, the antioxidant is vitamin E.

When UHMWPE is implanted in the body, macrophages attack the polymer and try to degrade it into smaller pieces. This is achieved by the production of hydrogen peroxide, which is a radical that reacts with the polymer and breaks the chains. The rate of this degradation process of the polymer in the body may be decreased by the addition of an antioxidant, which would act as a radical scavenger and react with the free radicals that are produced in the polymer due to the attack by the hydrogen peroxide. Thus, there are two major effects of the antioxidant. Firstly, it reduces the oxidation of the polymer due to $\gamma$-radiation, and, secondly, it decreases the degradation rate of the UHMWPE implant in the body.

According to the invention UHMWPE powder is doped with an antioxidant, preferably vitamin E, by mixing the UHMWPE particles with an antioxidant and a solvent comprising $CO_2$ under supercritical fluid conditions, a superfluid mixture being formed.

As a solvent for the antioxidant, $CO_2$ with supercritical properties is used. By performing the antioxidant doping of the UHMWPE particles in $CO_2$ above its critical pressure and temperature several advantages are obtained. The main advantage of the superfluid mixture obtained in the inventive method is that $CO_2$ with supercritical properties flows without viscosity, thus facilitating the transport into the UHMWPE particles of the antioxidant dissolved in the liquid fluid component of the superfluid mixture. Preferably, the temperature of the mixture is at least 50 C. and the pressure is at least 100 bar.

Thus, the antioxidant is dissolved in $CO_2$ under supercritical fluid conditions and added to the UHMWPE powder. The solution is forced into the pore system of the polymer particles by the pressure and depending on the $CO_2$ pressure and temperature, the UHMWPE polymer swells to different degrees in the $CO_2$, thus allowing the low molecular weight antioxidant dissolved in the liquid to diffuse into the UHMWPE matrix. When diffusion equilibrium is approached the pressure is lowered to below the critical pressure of $CO_2$, i e a condition where $CO_2$ is in the gaseous state. The $CO_2$ evaporates and leaves the polymer matrix and the interior of the polymer particles, leaving the antioxidant well dispersed in the polymer.

The antioxidant can also be mixed with the $CO_2$ under supercritical fluid conditions as a solution of an antioxidant as long as a superfluid mixture is obtained, and subsequently proceed as stated above.

Several parameters have an effect on the doped amount of antioxidant. Important parameters are temperature, pressure, treatment (mixing) time, and the rate of pressure release. The antioxidant concentration of the doped UHMWPE material can thus be controlled by changing a parameter for the antioxidant solubility in the superfluid mixture. The antioxidant concentration of the doped UHMWPE material can also be controlled by the amount of antioxidant initially mixed with the UHMWPE particles. The mixing of the superfluid mixture should be performed for at least 1 hour, preferably for at least 10 hours.

The most important parameters for controlling the antioxidant concentration of the doped UHMWPE material are the temperature and the pressure of a reactor, in which the inventive method is performed, since the solubility of an antioxidant is very much dependant if these parameters. For example, the solubility of vitamin E in $CO_2$ under supercritical fluid conditions follows the equation (Chrastil, Solubility of solids and liquids in supercritical fluids, Journal of Physical Chemistry 1982, 86 (15), p. 3016–3021):

$$c=d^{8.231}\times\exp[-17353.5/T+0.646]$$

in which c is the concentration (g/l) of vitamin E in $CO_2$; d is the density (g/l) of $CO_2$; and K is the temperature in Kelvin.

When taking in account the variation of the density of $CO_2$ as function of temperature and pressure (l'air liquide, Encyclopedie des gaz, p. 338) the solubility of the antioxidant in g/l of $CO_2$ is obtained as shown in FIG. 1 for the antioxidant vitamin E.

According to FIG. 1 the solubility of vitamin E in $C_2$ at 20 C. is very low, while it is much higher at 80 C. By carefully selecting the temperature and the pressure in the reactor a specific concentration of dissolved vitamin E in the superfluid mixture can be obtained thus controlling its concentration.

The temperature of the superfluid mixture and the mixing time are also important parameters for the diffusion and homogenization process. High temperatures result in higher diffusion rates, and a more homogenous distribution of the antioxidant in the UHMWPE particles is obtained the longer the mixing time. The antioxidant amount of the doped UHMWPE particles after the evaporation of $CO_2$ is thus controlled by choosing a pressure/temperature combination which corresponds to a suitable concentration of antioxidant dissolved in the $CO_2$.

The rate of pressure release is also important since if it is not controlled, the vitamin E can again be extracted from the particle when released.

The amount of antioxidant present in the UHMWPE after evaporation of the $CO_2$ should be approximately 0.005–5.0 weight %, preferably approximately 0.1–1.0 weights. The antioxidant can be deposited on the surface of and/or dispersed inside the UHMWPE particles.

UHMWPE doped with an antioxidant by the method of the invention has excellent properties for the manufacturing of implants, especially joint prostheses. The UHMWPE powder doped with antioxidant is compression molded either directly into implants or into blocks, from which implants are produced by mechanical processing, e g turning, etc. Finally, the implant having excellent wear resistance and markedly reduced degradation in the body are packaged and sterilized.

In order to further improve the wear resistance of UHMWPE or the implants, the antioxidant doped UHMWPE material may be subjected to γ- or β-radiation at a dose above 2 Mrad, preferably above 9 Mrad, followed by annealing (remelting), i e subjecting the UHMWPE particles or the implant to an elevated temperature, preferably above 80 C. when vitamin E is used. This procedure results in an increased crosslinking of the polymer, thereby enhancing the wear resistance thereof. This radiation/remelting treatment can be carried out at any stage in the manufacturing process; from powder to implant.

EXAMPLES

The invention will now be further described and illustrated by reference to the following examples. It should be noted, however, that these examples should not be construed as limiting the invention in any way.

FTIR

The concentration of vitamin E in the UHMWPE powder after doping was measured by means of Fourier Transform Infrared (FTIR) spectroscopy. The measurement was performed directly on the treated powder, and also after washing of the same (in toluene). The first measurement indicated that vitamin E is present on the surface of and/or inside the particle, whereas the measurement after washing indicated that vitamin E is present inside the particle.

ESR

Determination of free radical concentration was made by means of Electron Spin Resonance (ESR) at room temperature, immediately after and 1–60 days after γ-irradiation of 0–200 kGy. The concentration of radicals was measured on samples without vitamin E and with 0.5 weight % vitamin E.

Example 1

Ultra high molecular weight polyethylene (0.75 g; UHMWPE) as a powder (particles) of GUR 1120, medical grade for compression molding with a molecular weight of 3–4,000,000 g/mole and 39% crystallinity, was added to a reactor having a volume of 0.04 liters in a thermo-regulated bath. Vitamin E (1 g), which is a viscous dark amber oil, was then added to a calculated final concentration of about 1.9 g of vitamin E per 100 g of UHMWPE (1.9 weight %)

The temperature of the bath was increased to 80 C., after which gaseous $CO_2$ was pumped into the reactor to a pressure of 350 Bar, as controlled by a pressure meter. The mixture was kept at this temperature and pressure for 48 h. Then the pressure of the reactor was decreased, via a micro-valve connected to a flow meter, at a constant flow rate of $CO_2$ for a time period of 20 minutes, and the temperature of the bath was subsequently allowed to decrease until ambient conditions were obtained.

The doped UHMWPE powder had a slightly yellow color from the vitamin E content, and the color was visually homogeneous (the undoped UHMWPE powder is white). The UHMWPE power was also subjected to FTIR spectroscopy, and the vitamin E was found to be homogeneously distributed within the UHMWPE particles.

Example 2

HMWPE doped with vitamin E at a concentration of 0.5 weight % was prepared and compression moulded to blocks. Sample rods of 3×3×10 mm were then machined out from the blocks and were subjected to γ-irradiation at doses 0–200 kGy. UHMWPE samples without vitamin E were prepared in the same manner and irradiated at the same conditions. The concentration of free radicals present in the material was then meassured by means of ESR.

The results of the ESR are shown in Table 1, in which the radical concentration of pure UHMWPE and vitamin E doped UHMWPE samples is shown immediately after γ-irradiation and after approximately 1, 3, 5 and 9 weeks, respectively. Each result corresponds to the average value obtained from 4 different samples.

TABLE 1

| γ dose (kGy) | Vitamin E content | ESR 1 signal | ESR 2 signal | ESR 3 signal |
|---|---|---|---|---|
| 0 | 0 | 8.03 | | |
| 0 | 0.5% | 7.94 | | |
| 40 | 0 | 116.7 (0) | 7.80 (20) | 8.28 (61) |
| 40 | 0.5% | 11.45 (0) | 7.98 (20) | 8.60 (61) |
| 80 | 0 | 206.4 (0) | 10.72 (19) | 15.04 (60) |
| 80 | 0.5% | 17.09 (0) | 8.53 (19) | 15.00 (60) |
| 100 | 0 | 181.7 (0) | 38.3 (7) | 13.03 (38) |
| 100 | 0.5% | 20.8 (0) | 11.8 (7) | 15.46 (38) |
| 200 | 0 | 252.4 (0) | 95.7 (7) | 30.5 (35) |
| 200 | 0.5% | 66.2 (0) | 29.5 (7) | 29.80 (35) |

In table 1 it is clearly shown that the presence of 0.5 weight % vitamin E has a dramatic effect on the radiation induced radical concentration in UHMWPE immediately after γ-irradiation. Vitamin E almost completely eliminates the formation of radicals during γ-irradiation. There is, however, a small amount of radicals formed also in the UHMWPE samples with vitamin E.

What is claimed is:

1. A method for the preparation in a reactor of an antioxidant doped UHMWPE material to be used in an implant, said method comprising the steps of mixing UHMWPE particles with an antioxidant and a solvent comprising $CO_2$ under supercritical fluid conditions at elevated temperature and pressure, a superfluid mixture being formed, and after mixing the pressure is released from said reactor, $CO_2$ being evaporated from said mixture.

2. The method according to claim 1, wherein the temperature of said mixture is above the supercritical temperature for $CO_2$.

3. The method according to claim 2, wherein the temperature of said mixture in said reactor is at least 50 C.

4. The method according to claim 1, wherein the pressure in said reactor is above the supercritical pressure for $CO_2$.

5. The method according to claim 4, wherein the pressure in said reactor is at least 100 bar.

6. The method according to claim 1, wherein the concentration of said antioxidant in said doped UHMWPE material is controlled by changing a parameter for the antioxidant solubility in said superfluid mixture.

7. The method according to claim 6, wherein said parameter is the temperature in said reactor.

8. The method according to claim 6, wherein said parameter is the pressure in said reactor.

9. The method according to claim 5, wherein the concentration of said antioxidant in said doped UHMWPE material is controlled by the amount of said antioxidant mixed with said UHMWPE particles.

10. The method according to claim 9, wherein the concentration of said antioxidant in said doped UHMWPE material is about 0.005–5.0 weight %.

11. The method according to claims 10, wherein the concentration of said antioxidant in said doped UHMWPE material is about 0.1–1.0 weight %.

12. The method according to claim 9, wherein said mixing in said reactor is performed for at least 1 hour.

13. The method according to claim 12, wherein said mixing in said reactor is performed for at least 10 hours.

14. The method according to claim 13, wherein said antioxidant is vitamin E.

15. The method according to claim 14, wherein said vitamin E is α-tocopherol.

16. The method according to claim 15, wherein said antioxidant doped UHMWPE material is γ-irradiated at a dose of at least 2 Mrad.

17. The method according to claim 16, wherein said dose is at least 9 Mrad.

18. The method according to claim 17, wherein the temperature of said antioxidant doped UHMWPE material is raised after the γ-irradiation.

19. The method according to claim 18, wherein the temperature is raised to a least 80 C.

* * * * *